(12) United States Patent
Stenzel

(10) Patent No.: US 6,939,318 B2
(45) Date of Patent: Sep. 6, 2005

(54) METHOD, TOOL, AND SYSTEM FOR DEPLOYING AN IMPLANT INTO THE BODY

(75) Inventor: Eric B. Stenzel, Tuam (IE)

(73) Assignee: Boston Scientific SciMed, Inc., Maple Grove, MN (US)

(*) Notice: Subject to any disclaimer, the term of this patent is extended or adjusted under 35 U.S.C. 154(b) by 48 days.

(21) Appl. No.: 10/001,960

(22) Filed: Dec. 5, 2001

(65) Prior Publication Data

US 2003/0208153 A1 Nov. 6, 2003

(51) Int. Cl.⁷ .............................................. A61M 31/00
(52) U.S. Cl. ........................................ 604/60; 604/506
(58) Field of Search ............................ 604/59, 57, 60, 604/61, 93.01, 104, 174, 58, 63, 64, 106, 107, 167.06, 170.01, 170.02, 235, 294, 264, 502, 506.07, 509, 96.01, 164.01–164.09, 164.1, 164.11; 623/612; 606/107, 108, 167, 185, 191, 198, 139

(56) References Cited

U.S. PATENT DOCUMENTS

| | | | |
|---|---|---|---|
| 5,156,609 A | * | 10/1992 | Nakao et al. ............... 606/142 |
| 5,752,970 A | | 5/1998 | Yoon |
| 6,183,444 B1 | | 2/2001 | Glines et al. ............... 604/187 |
| 6,183,485 B1 | | 2/2001 | Thomason et al. |
| 6,197,324 B1 | | 3/2001 | Crittenden ................. 424/423 |
| 6,436,068 B1 | * | 8/2002 | Bardy .......................... 604/57 |
| 6,497,651 B1 | * | 12/2002 | Kan et al. .................. 600/114 |

* cited by examiner

Primary Examiner—Kevin C. Sirmons
(74) Attorney, Agent, or Firm—Kenyon & Kenyon

(57) ABSTRACT

In one embodiment of the present invention a system for maneuvering an implant to a target site and deploying the implant at the target site is provided. This system includes an inner housing and an outer housing where the inner housing is slidable within the outer housing. The outer housing may have a working channel with a first end and a second end and a piercing jaw moveably coupled to the first end. The inner housing may have a working passage with a distal end and a proximal end, the distal end having a piercing jaw moveably coupled to it.

19 Claims, 4 Drawing Sheets

METHOD, TOOL, AND SYSTEM FOR DEPLOYING AN IMPLANT INTO THE BODY

TECHNICAL FIELD

The present invention regards the delivery of an implant. More specifically, the present invention regards the deployment of an implant near a target site in the body of a patient after manipulating and moving the implant through the body without the need for an internal lumen of the body.

BACKGROUND

The deployment of an implant in the body is an often repeated and advantageous procedure performed during the practice of modern medicine. Implants may be used for innumerable purposes including the delivery of therapeutic for short and prolonged periods of time and for the structural support of failing internal cavities and lumens. Implants may be deployed in either case through non-invasive procedures such as endoscopy and through more invasive procedures that require large incisions into the body of a patient. The non-invasive and less-invasive procedures are generally used when the target area is accessible through a lumen of the body while the more invasive procedures may be employed when the target area is located deep within the body or otherwise not readily accessible through a lumen of the body.

Invasive procedures have a higher financial cost and inflict a greater amount of trauma to the patient than non-invasive procedures. Consequently, non-invasive procedures are generally preferred over invasive procedures when given the choice. In certain circumstances, however, it may not be efficient or plausible to perform a procedure non-invasively. In these circumstances, more-invasive procedures may be required despite their shortcomings. For instance, when an implant needs to be deployed deep into the body in an area that is not readily accessible through a lumen or an external orifice an invasive procedure may be the only plausible technique. Similarly, when the target area is located deep within a muscle or tissue that does not have a nearby or sufficiently large lumen to provide access to the target site an invasive procedure may, again, be the only plausible technique. Consequently, in these situations as well as in others, a practitioner may be left with no choice but to perform an invasive procedure to deploy the implant to the targeted area.

SUMMARY OF THE INVENTION

In one embodiment of the present invention a system for maneuvering an implant to a target site and deploying the implant at the target site is provided. This system includes an inner housing and an outer housing where the inner housing is slidable within the outer housing. The outer housing may have a working channel with a first end and a second end and a piercing jaw moveably coupled to the first end. The inner housing may have a working passage with a distal end and a proximal end, the distal end having a piercing jaw moveably coupled to it.

A device for maneuvering an implant to a target site in the body and deploying the implant at the target site is provided in an alternative embodiment of the present invention. This device may have a housing that may contain a working channel, an outside surface, a first end, and a second end with a first piercing jaw being moveably coupled to the first end of the housing. This piercing jaw may be moveable from a first closed position to a second open position wherein the second open position allows access to the working channel of the housing.

A method for maneuvering an implant to a target site and deploying the implant at the target site is provided in another alternative embodiment of the present invention. The method in this embodiment includes: guiding a first housing having a piecing jaw and a working channel through the body to a target site in the body; urging a second housing from an end of the working channel of the first housing; retracting the second housing into the working channel of the first housing; and, deploying an implant at the target site.

DETAILED DESCRIPTION

Figure 1:
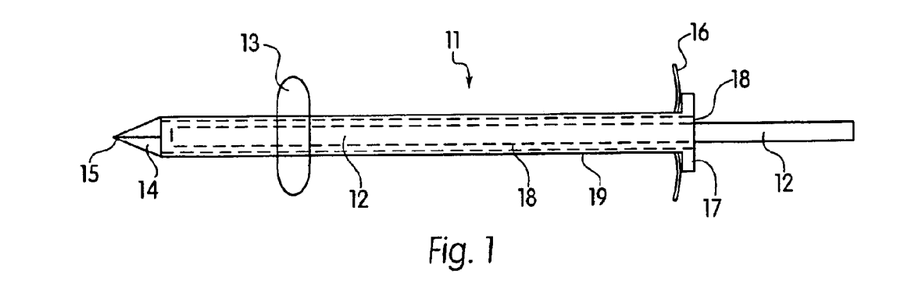
FIG. 1 is a side view of an outer housing in accord with one embodiment of the present invention.

FIG. 1 is a side view of an outer housing 11 as may be used to deploy an implant at a target area within the body of a patient in accord with one embodiment of the present invention. The outer housing 11 in this embodiment may be made from any biocompatible material. This material is preferably flexible enough to allow the outer housing 11 to be pushed into the body in conjunction with a guide wire placed therein. The main shaft of this housing 11 may be more rigid than the distal tip to allow for better pushability. As can be seen, the outer housing 11 in this embodiment contains a grip 16 located at the proximal end of the outer housing 11, a locking collar 17 also located at the proximal end of the outer housing 11, and a working channel 18 located within the outer housing 11 wherein the working channel 18 allows passage through the outer housing 11 from its proximal end to its distal end. Also evident in FIG. 1 is the expandable bladder 13 positioned and secured to the outside surface 19 of the outer housing 11 and the piercing jaws 14 that terminate in a piercing tip 15 located at the distal end of the outer housing 11. The outer housing 11 in FIG. 1 is illustrated with a guide wire 12 located in its working channel 18. This guide wire 12 is positioned within the working channel 18 and may be used by a practitioner to guide and steer the outer housing 11 within the body of a patient. Then, once the distal end of the outer housing 11 has reached the target site, the guide wire 12 may be removed to allow the practitioner to use the working channel 18 of the outer housing 11. The guide wire 12 may be any common guide wire known to one of skill in the art. It may be controlled by the practitioner from the proximal end of the housing, by the portion of the wire 12 that extends out of the housing or by any other mechanism known to and commonly used by one of skill in the art.

The piercing jaws 14, which terminate in a piercing tip 15, may be preferably made from stainless steel, and may be shaped to form a cone when they are in their closed position. Alternatively, the jaws 14 may be made from a radiopaque material or from tantalum. Moreover, they may be coated to allow them to deliver a therapeutic when in use. They may also be covered with a radiopaque or other coating such as gold to allow for the more effective tracking of the jaws during their use.

The piercing jaws 14 may be pivotally connected to the distal end of the housing 11 such that they may open or pivot about their connection points. When the piercing jaws 14 are in a closed position they may assist the outer housing 11 in burrowing through tissue and muscle as the outer housing 11 is pushed and maneuvered with a guide wire by a practitioner during its insertion. Then, upon reaching the target site, the jaws 14 may open to provide access to the target area from the working channel 18. In order to assist in stabilizing the outer housing 11, after it has reached the target site (or at any other point in the process), the expandable bladder 13, located on the external surface 19 of the outer housing 11, may be inflated to temporarily secure the outer housing 11 within its surroundings. This bladder may be inflated through the use of an inflation port (which is not shown) located at the proximal end of the housing that is in fluid communication with the bladder via a channel in the housing (which is not shown). As described in more detail below, this expandable bladder may be treated or covered with a therapeutic designed to assist in the procedure.

Figures 2, 3:
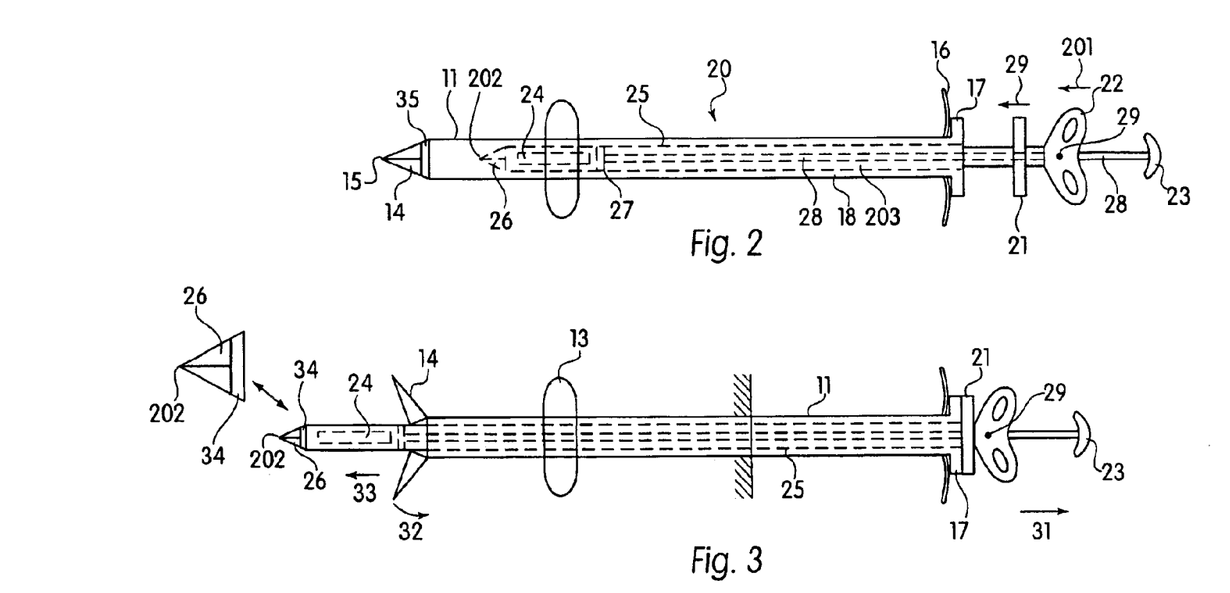
FIG. 2 is a side view of an implant system employing the outer housing from FIG. 1 in accord with an alternative embodiment of the present invention.
FIG. 3 is a side view of the implant system from FIG. 2 being used to deploy an implant at a target area of the body in accord with an alternative embodiment of the present invention.

FIG. 2 is a side view of an implanting system 20 that may be used to deploy implants at a target site in the body in accord with an alternative embodiment of the present invention. The system 20 in this embodiment employs the outer housing 11 from FIG. 1. This system 20 also employs an inner housing 25, the inner housing having piercing jaws 26 that end in a piercing tip 202. In addition, the inner housing 25 has a locking collar 21, a handle 22, a band 35, and a knob 23. The knob 23 in this embodiment is coupled to a plunger shaft 28 that is itself coupled to a plunger head 27. Therefore, when the knob 23 is slid within the inner housing 25 the plunger head 27, urged by the plunger shaft 28, slides along with it. Like the outer housing 11 the inner housing 25 may be made from any suitably rigid material including flexible plastics and hard rubbers while the knob 23 and the plunger assembly (the shaft 28 and the head 27) may be made from a more rigid material such as stainless steel and various polymers.

In the embodiment of FIG. 2 an implant 24 has been loaded into the working passage 203 of the inner housing 25. This implant may contain therapeutic for delivery to the target site or may be designed to perform some specific function for the target area. The system 20 of FIG. 2 may, therefore, be used to deploy the implant 24 to a target area by a practitioner using the system.

As is apparent the inner housing 25 is sized in this embodiment to fit within the working channel 18 of the outer housing 11. Consequently, the inner housing 25 may readily slide back and forth within the outer housing 11.

The system 20 of FIG. 2 may be used by first inserting and guiding the outer housing 11 into the body of a patient and to the target site using a guide wire or other control device as described above. Once the distal end of the outer housing has reached the target site the guide wire or other control device may then be removed. In conjunction with the distal end reaching the target site the expandable bladder 13 may be expanded by forcing fluid into it through a second channel (illustrated in FIG. 5) in the outer housing. The inner housing 25 may then be inserted into the working channel 18 of the outer housing 11 until the locking collar 21 of the inner housing 25 meets the locking collar 17 of the outer housing 11. These collars may then be connected to one another such that the inner housing 25 and the outer housing 11 are fixed relative to one another during the procedure. When the locking collars are engaged, knob 23 may remain in a fixed position to both collars because handle 22 may be held in a fixed position by pin 29 which passes through shaft 28.

As can be seen in FIG. 3, which is a side view of the implanting system 20 of FIG. 2, the length of the inner housing 25 may be longer than the outer housing 11. Consequently, when the locking collars are connected to one another the inner housing 25 protrudes out from the distal end of the outer housing 11. As is evident, when the inner housing 25 protrudes out through the outer housing 11 the piercing jaws 14 open and swing away from the outer housing 11.

Figure 4:
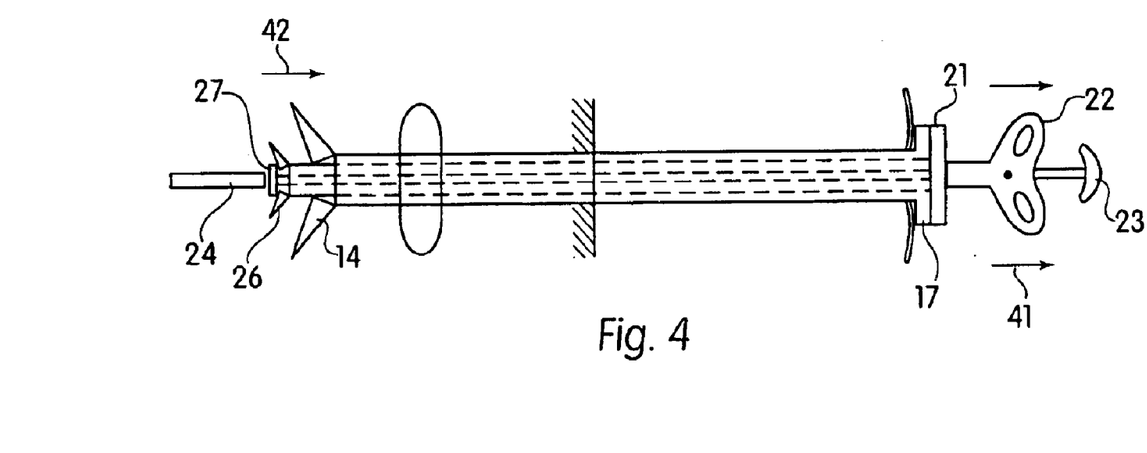
FIG. 4 is a side view of the implant system from FIG. 2 as the inner housing is being retracted back into the outer housing and the implant is being deployed in accord with an alternative embodiment of the present invention.

Once the distal end of the system 20 has reached the target area a practitioner may remove the locking pin 29 and pull handle 22 proximally towards knob 23 as indicated by arrow 31 of FIG. 3 and arrows 41 of FIG. 4. As can be seen in FIG. 4, as handle 22 is withdrawn the inner housing will 25 retract in the direction of arrow 42 into the outer housing 11. As the inner housing is retracted the jaws 26 will close not only from the force of the band 34 but also from the force of the inner housing 25 being withdrawn into the outer housing 11.

The head 27 in this embodiment is held in a fixed position by and is connected to knob 23. The purpose of head 27 is to hold the implant 24 in the desired position while inner housing 25 is retracted into the outer housing 11, thus allowing the implant to be deployed at the specific desired location.

Band 34 in this embodiment, which is only shown in FIG. 3, may be located on the proximal section of the piercing jaws 26 and may be made from an elastic material. This band 34 serves to hold the piercing jaws closed while the device is being positioned in addition to allowing the jaws to open when the inner housing 25 is extended from the outer housing 11 during deployment.

Thus, in use, inner housing 25 is pushed through outer housing 11 until the proximal end of implant 24 is distal to the piercing tip 15. At this point, locking collar 21 is engaged to collar 17 to hold the implant 24 in the desired location. Then, the practitioner may place a thumb on the distal end of knob 23 and, using his fingers, pull handle 22 towards knob 23 to retract inner housing 25 into outer housing 11.

During this step, the implant 24 is held in its desired position by head 27 which is connected to knob 23. After the piercing tip 202 has been retracted past the implant 24 the band 34 will assist in closing the jaws 26. At this point the implant will have been deployed and the locking collars 17 and 21 may be released so that the inner housing 25 may be removed from the working channel 18. As the inner housing 25 is retracted from the outer housing 11 the jaws 14 of the outer housing will close under the closing force of the elastic band 35, which is illustrated in FIG. 2.

Once the implant 24 has been deployed the entire system 20 may be retracted out of the patient or the inner housing 25 may be retracted out of the working channel 18 and a second inner housing 25 may be inserted into the working channel 18 so that a second implant may be deployed at the target site or at a different target site either along the same initial entry path or along a different entry path. Alternatively, the inner housing may contain several implants that may be implanted without retracting the system or the inner housing from the patient. Furthermore, the outer housing may be retracted slightly and an implant may be deployed in this second position.

The implants that may be deployed in accord with the various embodiments of the present invention include therapeutic laden implants and structural implants that include: expandable and self expanding stents, balloon catheters, vena-cava filters, aneurysm coils, stent-grafts, a-v shunts, angio-catheters, and PICC's. Moreover, these implants as well as others may be treated with a wide variety of therapeutics which include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/ antiproliferative/antimitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin, anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidemial growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors; anti-restenosis agents, including p15, p16, p18, p19, p21, p27, p53, P57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

These therapeutic agents can be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy, congestive heart failure or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, for treating congestive heart failure and other muscle degradation or damage, and for inducing nerve, blood vessel or tissue regeneration in a particular tissue or organ.

Figure 5:
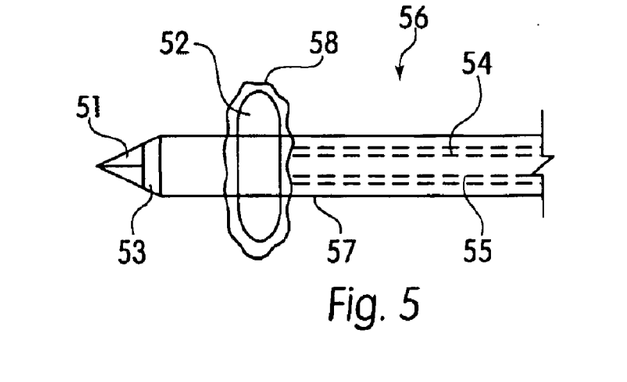
FIG. 5 is an enlarged side view of the distal end of a housing in accord with another alternative embodiment of the present invention.

FIG. 5 is a distal side view of a housing 56 that may be used on an inner or outer housing in the systems described above in accord with an another alternative embodiment of the present invention. In this alternative embodiment the piercing jaws 51 have been held together with a biasing element 53. This biasing element 53 may be a rubber band or any other elastic material that may cause the piercing jaws 51 to remain in a closed position during the movement of the housing 56 to the target site and may then cause the jaws 51 to close after an implant has been deployed or an inner housing has been retracted back inside of it.

As can be seen in this embodiment, the outside surface of the piercing jaws 51 have been recessed such that the surface of the biasing element 53 is flush with the surface of the piercing jaws 53. Also evident in FIG. 5 is the expandable bladder 52, which may have been coated with a coating 58 that may contain a therapeutic. The housing 56 in this embodiment may also contain a fluid channel 55 and a therapeutic channel 54. The fluid channel 55 may be used to inflate and deflate the bladder 52 while the therapeutic channel 54 may be used to pump therapeutic to the target area or to the surface of the bladder 52 during the procedure. In each case, the therapeutic employed may include the therapeutics listed above as well as any other suitable therapeutic.

Figure 6:
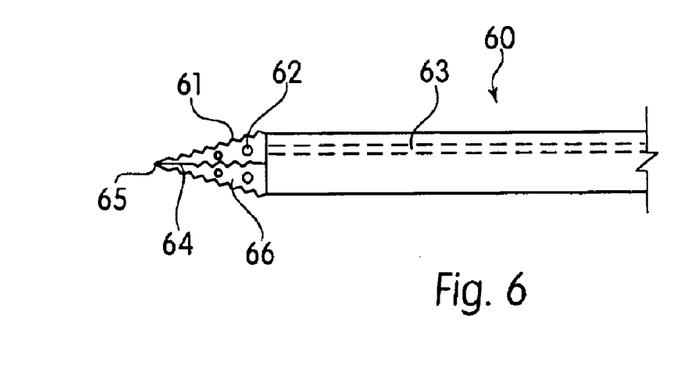
FIG. 6 is an enlarged side view of the distal end of a housing in accord with another alternative embodiment of the present invention.

FIG. 6 is a side view of the distal end of a housing 60 in accord with another alternative embodiment of the present invention. The housing 60 in this embodiment may be employed as an internal or an external housing in the systems described above. In the embodiment of FIG. 6 the piercing jaws 66 may have a serrated surface 61 and a plurality of orifices 62 on them. The jaws 66, which end in a piercing tip 65, are separable along a serrated interface line 64. The orifices 62 in the jaws 66 may be in fluid communication with a second internal channel 63 that may be used to provide therapeutic or any other fluid to the target area. Alternatively, these orifices 62 may also be used to draw fluid from the target area.

In each of the above described embodiments the piercing jaws have been separable into two sections about an interface line. However, other configurations are also plausible as the piercing jaws may be separable into three or more sections and may even not be separable at all, instead, having a single jaw that pivots to one side to allow access to the passage or channel of the housing.

Figure 7:
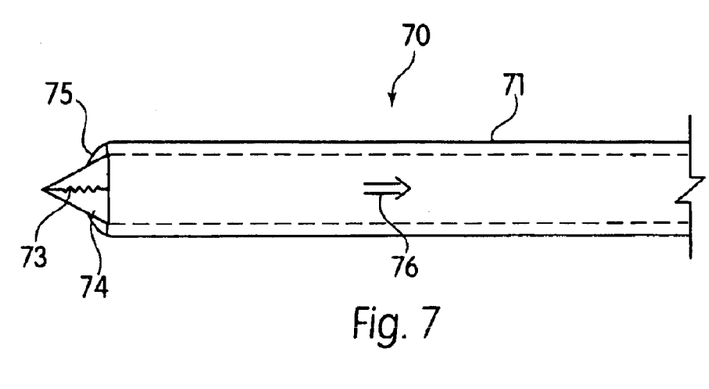
FIG. 7 is an enlarged side view of the distal end of an inner housing in accord with another alternative embodiment of the present invention.

FIG. 7 is a side view of a housing 70 in accord with another alternative embodiment of the present invention. The housing 70 in this embodiment has an extension sleeve 71 surrounding at least a portion of it. This extension sleeve 71 may be connected to a connecting or extension line 75 which is in turn connected to the piercing jaws 74. When the extension sleeve is slid in the direction of arrow 76 the piercing jaws will open, thereby allowing the housing to grab and hold an implant or other object as required.

Figure 8:
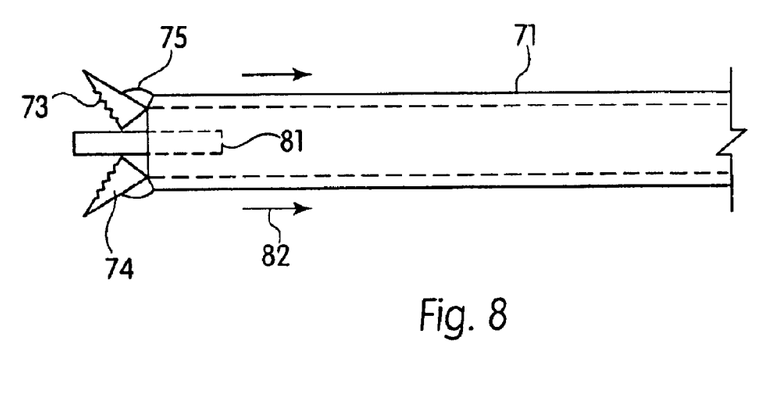
FIG. 8 is an enlarged side view of the inner housing of FIG. 7 as it may be used to retrieve an implant in accord with another alternative embodiment of the present invention.

FIG. 8 is a side view of the housing 70 from FIG. 7. As can be seen in FIG. 7 the sleeve 71 has been slid and the jaws 74 have been opened and are shown grasping the implant 81. As can also be seen the jaws 74 have serrated edges 73 that help to grasp the implant 81 as it is retracted in the direction of arrows 82. The serrated edges 73 and the orientation of the jaws 74 may be configured as in FIG. 8 to help grasp the implant during the removal process.

Figure 9:
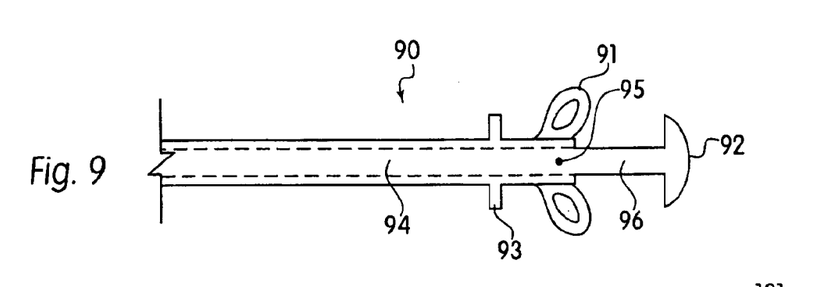
FIG. 9 is an enlarged side view of the proximal end of a single use inner housing in accord with another alternative embodiment of the present invention.

FIG. 9 is an enlarged view of the proximal end of a single use implanter in accord with another alternative embodiment of the present invention. In FIG. 9 an inner housing 90 or single use implanter having a knob 92, a plunger 96, a pin 95, a grip 91, a locking tee 93, and an inner lumen 94 is shown. The plunger 96 and the knob 92 may be preferably attached to one another and may be preferably slidable back and forth past the grip 91 and the locking tee 93 in the lumen 94. The pin 95, which may pass through holes in the plunger and knob assembly and the grip 91, may be used to lock the plunger and knob assembly to the grip 91 and to prevent them from moving relative to one another.

Figure 10:
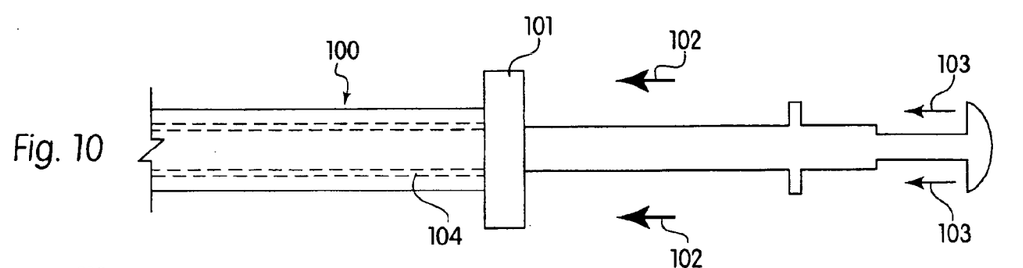
FIG. 10 is an enlarged side view of the proximal end of a single use inner housing placed within the proximal end of an outer housing.

FIG. 10 is a side view of the proximal end of the single use implanter from FIG. 9 placed within an outer housing 100. This outer housing 100 may contain lumen 104 that allows the inner housing 90 to slide back and forth within it. During use, after the distal end of the outer housing 100 has been placed at the target site in accord with procedures described above, the inner housing may be slid into the outer housing. This movement is identified by arrows 102. Then, when the implant located at the distal end of the inner housing needs to be deployed the inner housing may be pushed into the outer housing until the locking tee reaches the locking collar 101. At this point the piercing jaws located at the distal end of the inner housing will be preferably protruding out from the piercing jaws of the outer housing as described above. Then, in order to deploy the implant, the locking collar may be locked into the grooves 110 of the locking collar, the pin 95 may be removed from holes in the housings, and the knob 92 and plunger 96 may be pushed to deploy the implant from within the inner housing as described above. Alternatively, the locking tee and the locking collar may be mated but not locked together and the knob and plunger may be pushed.

As described above, once the implant has been deployed the inner housing 90 may then be removed, the outer housing may be repositioned to a new location, and the implant procedure may be repeated as above with a new single use implanter or inner housing. Alternatively, the inner housing may contain a second implant that may be deployed without removing the inner housing entirely from the outer housing.

Figure 11:
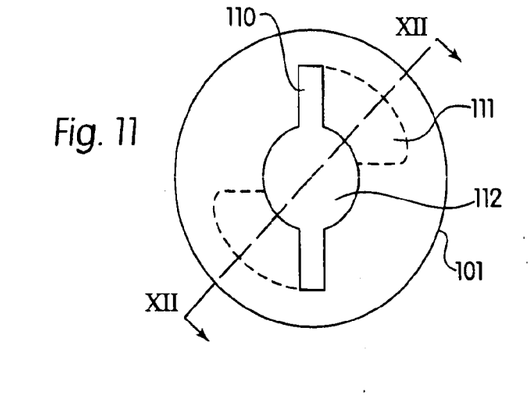
FIG. 11 is a plan view of the locking collar of FIG. 10.

FIG. 11 is a plan view of the locking ring 101. In FIG. 11 the slot 110, groove 111, and hole 112 can all be seen. This slot and groove configuration allows the locking tee 93 to be slid into the locking ring 101 and then rotated to lock the inner housing and the outer housing together during the procedure.

Figure 12:
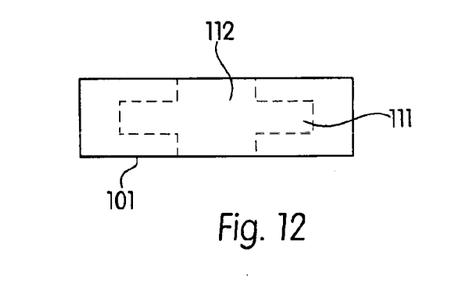
FIG. 12 is a cross-sectional view of the locking collar of FIG. 11 taken along line XII—XII of FIG. 11.

FIG. 12 is a cross-sectional view taken along line XII—XII of FIG. 11 that clearly shows the groove 111 within the locking ring 101.

While several embodiments of the present invention have been presented above, others, also within the spirit and scope of the invention may also be plausible. For example, in each of the above embodiments, a vacuum source may be in fluid communication with the working passage or channel of the housing to facilitate the removal of material from the target area.

What is claimed is:

1. A system for maneuvering an implant to a target site and deploying the implant at the target site, the system comprising:
   an outer housing having a working channel and first and second ends,
      the first end having a piercing jaw, the piercing jaw moveably coupled to the first end,
      the second end providing access to the working channel of the outer housing; and
   an inner housing having a working passage and distal and proximal ends,
      wherein the inner housing is sized to be slidable within the working channel of the outer housing, has a piercing jaw that is moveably coupled to the distal end of the inner housing, and has a plunger face positioned within the inner housing's working passage.

2. The system of claim 1 wherein the plunger face is slidable within the working passage of the inner housing.

3. The system of claim 1 wherein the outer housing contains a second internal channel.

4. The system of claim 1 wherein the outer housing an expandable bladder in physical communication with its external surface, the bladder expandable from a first position to a second larger position.

5. The system of claim 4 wherein an accessible surface of the bladder is covered with a therapeutic.

6. The system of claim 1 wherein the piercing jaw of the inner housing is separable into at least two sections.

7. The system of claim 6 wherein the two sections are biased towards each other with a biasing element.

8. The system of claim 1 wherein the working passage of the inner housing is in fluid communication with a vacuum source.

9. The system of claim 1 wherein the outer housing has a first locking collar in physical communication with its outside surface and the inner housing has a second locking collar in physical communication with its outside surface, and wherein the first locking collar and the second locking collar are releasably connected to one another.

10. The system of claim 1 wherein the plunger assembly is releasably coupled to either the first locking collar or the second locking collar.

11. A device for maneuvering an implant to a target site in the body and deploying the implant at the target site, the device comprising:
   a biocompatible housing having a working channel, an outside surface, a first end, and a second end;
   a first piercing jaw that is moveably coupled to the first end of the housing, ends in a piercing tip, and is moveable from a first closed position to a second open position, the second open position allowing access to the working channel of the housing; and
   an expandable bladder, the expandable bladder in physical communication with an outside surface of the housing, the expandable bladder from a first position to a second position.

12. The device of claim 11 wherein the expandable bladder is coated with a therapeutic.

13. The device for maneuvering an implant to a target site in the body and deploying the implant at the target site, the device comprising:
   a biocompatible housing having a working channel, a therapeutic channel, an outside surface, a first end, and a second end;
   a first piercing jaw that is moveably coupled to the first end of the housing, ends in a piercing tip, and is moveable from a first closed position to a second open position, the second open position allowing access to the working channel of the housing; and
   an expandable bladder having an inside and outside surface, the expandable bladder in physical communication with an outside surface of the housing, the outside surface of the expandable bladder in fluid communication with the therapeutic channel, the expandable bladder expandable from a first position to a second position.

14. A device for maneuvering an implant to a target site in the body and deploying the implant at the target site, the device comprising:
   a biocompatible housing having a working channel, an outside surface, a first end, and a second end;
   a first piercing jaw that is moveably coupled to the first end of the housing, ends in a piercing tip, and is moveable from a first closed position to a second open position, the second open position allowing access to the working channel of the housing; and
   a plunger assembly containing a plunger head and a plunger shaft, the plunger shaft terminating in a knob, the plunger shaft defining one or more holes, the plunger assembly located within the working channel of the housing.

15. A device for maneuvering an implant to a target site in the body and deploying the implant at the target site, the device comprising:
   a biocompatible housing having a working channel, an outside surface, a first end, and a second end;
   a first piercing jaw that is moveably coupled to the first end of the housing, ends in a piercing tip, and is moveable from a first closed position to a second open position, the second open position allowing access to the working channel of the housing; and
   a locking collar in physical communication with the outside surface of the housing.

16. A method for maneuvering an implant to a target site and deploying the implant at the target site, the method comprising:
   guiding a first housing having a piercing jaw ending in a piercing tip and a working channel through a body and to a target site in the body, the piercing tip forging the path towards the target in which the housing will travel;
   urging a second housing from an end of the working channel of the first housing;
   retracting the second housing into the working channel of the first housing;
   deploying an implant at the target site; and
   inflating an expandable bladder located around at least the first or second housing.

17. A method for maneuvering an implant to a target site and deploying the implant at the target site, the method comprising:
   guiding a first housing having a piercing jaw ending in a piercing tip and a working channel through a body and to a target site in the body, by manipulating a guide wire placed within the first housing;

urging a second housing from an end of the working channel of the first housing;

retracting the second housing into the working channel of the first housing; and deploying an implant at the target site.

18. A method for maneuvering an implant to a target site and deploying the implant at the target site, the method comprising:

guiding a first housing having a piercing jaw ending in a piercing tip and a working channel through a body and to a target site in the body;

urging a second housing from an end of the working channel of the first housing;

retracting the second housing into the working channel of the first housing;

deploying an implant at the target site; and releasably coupling a locking collar from the first housing to a locking collar from the second housing.

19. A system for maneuvering an implant to a target site and deploying the implant at the target site, the system comprising:

an outer housing having a working channel, and a first end and a second end, the first end having a first means for piercing into the body the first means for piercing moveably coupled to the first end, the second end providing access to the working channel of the outer housing; and an inner housing having a working passage and a distal end and a proximal end, wherein the inner housing is also sized to be slidable within the working channel of the outer housing and has a second means for piercing into the body that is moveably coupled to the distal end of the inner housing, the inner housing also having a plunger assembly positioned within its working passage.

\* \* \* \* \*